(12) United States Patent
Ohishi

(10) Patent No.: US 7,756,324 B2
(45) Date of Patent: *Jul. 13, 2010

(54) 3-DIMENSIONAL IMAGE PROCESSING APPARATUS

(75) Inventor: Satoru Ohishi, Otawara (JP)

(73) Assignees: Kabushiki Kaisha Toshiba, Tokyo (JP); Toshiba Medical Systems Corporation, Otawara-shi (JP)

(*) Notice: Subject to any disclaimer, the term of this patent is extended or adjusted under 35 U.S.C. 154(b) by 971 days.

This patent is subject to a terminal disclaimer.

(21) Appl. No.: 11/282,657

(22) Filed: Nov. 21, 2005

(65) Prior Publication Data

US 2006/0132483 A1 Jun. 22, 2006

(30) Foreign Application Priority Data

Nov. 24, 2004 (JP) ............................ 2004-339061

(51) Int. Cl.
*G06K 9/00* (2006.01)
(52) U.S. Cl. ...................... 382/154; 382/128; 345/419
(58) Field of Classification Search ................ 382/130, 382/128, 129, 131, 132, 154; 345/419, 619, 345/420–427; 348/42–60; 356/12–14
See application file for complete search history.

(56) References Cited

U.S. PATENT DOCUMENTS 5,647,360 A * 7/1997 Bani-Hashemi et al. ..... 382/130
5,839,440 A * 11/1998 Liou et al. ................... 600/431
7,330,573 B2 * 2/2008 Mielekamp ................. 382/128
2005/0046644 A1 3/2005 Ohishi

FOREIGN PATENT DOCUMENTS

JP 5-137711 6/1993
JP 2005-80285 3/2005

OTHER PUBLICATIONS

Qin Binjio Zhuang Tiango, "Use of Collation/Similarity Multi-Discrimination MR and CT Medical Imaging Method" Chinese Journal of Biomedical Engineering, vol. 22, No. 1, Feb. 2003, pp. 1-5 & 11.

* cited by examiner

Primary Examiner—Aaron W Carter
(74) Attorney, Agent, or Firm—Oblon, Spivak, McClelland, Maier & Neustadt, L.L.P.

(57) ABSTRACT

A three-dimensional image processing apparatus includes a storage unit that stores data of a plurality of mask images obtained by radiographing a subject to be examined in a different direction before contrast medium injection and data of a plurality of contrast images obtained by radiographing the subject to be examined in a different direction after the contrast medium injection, a reconstruction unit that reconstructs first three-dimensional image data from the plurality of mask image data and second three-dimensional image data from the plurality of contrast image data, a positional deviation correcting unit that corrects positional deviation of the first three-dimensional image with respect to the second three-dimensional image based on comparison between an anatomical structure of the first and second three-dimensional image data, and creates third three-dimensional image data, and a processing unit that performs subtraction between the second and the third three-dimensional data and creates fourth three-dimensional image data.

20 Claims, 9 Drawing Sheets

3-DIMENSIONAL IMAGE PROCESSING APPARATUS

CROSS-REFERENCE TO RELATED APPLICATIONS

This application is based upon and claims the benefit of priority from prior Japanese Patent Application No. 2004-339061, filed Nov. 24, 2004, the entire contents of which are incorporated herein by reference.

BACKGROUND OF THE INVENTION

1. Field of the Invention

The present invention relates to a three-dimensional image processing apparatus that creates a three-dimensional image of a blood vessel from images before and after contrast medium injection.

2. Description of the Related Art

Blood vessels of a head extend in a complicated manner. For example, in a case of an aneurysm, in order to determine an optimal observation angle capable of confirming a neck of the aneurysm or obtain a relationship between the neck and a dome, or the aneurysm and the blood vessel/a capillary vessel near the aneurysm, 3D-DSA (three-dimensional digital subtraction angiography) is generally carried out.

In the 3D-DSA, the patient is repeatedly radiographed while rotating an X-ray tube around the patient, and a plurality of images each of which is obtained by radiographing the patient in a different direction are collected before or after contrast medium injection. Generally, a two-dimensional projection image, which is collected before contrast medium injection such that the blood vessel is not contrasted, is called a mask image, and a two-dimensional projection image, which is collected after the contrast medium injection such that the blood vessel is contrasted, is called a contrast image. By radiographing a subject at predetermined positions, an image before contrast medium injection and an image after the contrast medium injection are subtracted, so that the contrasted blood vessel portion is mainly extracted. In addition, a three-dimensional reconstruction process is performed on the extracted image of the blood vessel portion, so that a detailed three-dimensional image of the blood vessel is created. This three-dimensional image is called a 3D-DSA image.

As is widely known, the injection of the contrast medium imposes a negative side effect on the patient. In particular, at the time of an angiogram examination of a head, the moment the injection of the contrast medium starts, the patient may feel intense heat on his head, causing unbearable pain for the patient. As a result, the moment the contrast medium starts to be injected into the head of the patient, the patient moves his head. In order to prevent the patient from moving his head, the head of the patient is held in position by a belt. If the head of the patient is held in position tightly by the belt, the belt causes the patient to feel pain. Therefore, it is very difficult to completely prevent the patient from moving his head. Due to this reason, the biogenic positions in the frames are likely to deviate between the mask image and the contrast image. This positional deviation may appear on the 3D-DSA images as artifacts.

In order to reduce the artifact caused by the positional deviation, it has been considered that the positional deviation between the mask image and the contrast image is corrected and the subtraction is then performed between the mask image and the contrast image. However, actually, due to the positional deviation being a three-dimensional displacement, a reduction effect of the artifacts through the positional deviation correction is not very effective (for example, see JP-A-5-137711 and JP-A-2005-80285).

BRIEF SUMMARY OF THE INVENTION

Accordingly, it is an object of the present invention to provide a three-dimensional image processing apparatus capable of creating a three-dimensional image of a blood vessel from an image before or after contrast medium injection, and improving a reduction effect of an artifact caused by the movement of a subject to be examined before or after the contrast medium injection.

According to a first aspect of the invention, there is provided a three-dimensional image processing apparatus which includes a storage unit that stores data of a plurality of mask images and data of a plurality of contrast images, each of the plurality of mask images being obtained by radiographing a subject to be examined in a different direction before contrast medium injection, each of the plurality of contrast images being obtained by radiographing the subject to be examined in a different direction after the contrast medium injection; a reconstruction unit that reconstructs first three-dimensional image data from the plurality of mask image data and reconstructs second three-dimensional image data from the plurality of contrast image data; a positional deviation correcting unit that corrects positional deviation of the first three-dimensional image with respect to the second three-dimensional image on the basis of the comparison result between an anatomical structure of the first three-dimensional image data and an anatomical structure of the second three-dimensional image data, and creates third three-dimensional image data; and a processing unit that performs subtraction between the second three-dimensional image data and the third three-dimensional data and creates fourth three-dimensional image data.

According to a second aspect of the invention, there is provided a three-dimensional image processing apparatus which includes a storage unit that stores data of a plurality of mask images and data of a plurality of contrast images, each of the plurality of mask images being obtained by radiographing a subject to be examined in a different direction before contrast medium injection, each of the plurality of contrast images being obtained by radiographing the subject to be examined in a different direction after the contrast medium injection; a reconstruction unit that reconstructs first three-dimensional image data from the plurality of mask image data and reconstructs second three-dimensional image data from the plurality of contrast image data; a positional deviation amount calculating unit that calculates a positional deviation amount of the first three-dimensional image with respect to the second three-dimensional image on the basis of the comparison result between a partial region of the first three-dimensional image data and a partial region of the second three-dimensional image data; a positional deviation correcting unit that corrects the first three-dimensional image on the basis of the calculated positional deviation amount and creates third three-dimensional image data, and a processing unit that performs subtraction between the second three-dimensional image data and the third three-dimensional image data and creates fourth three-dimensional image data.

According to a third aspect of the invention, there is provided a three-dimensional image processing apparatus which includes a storage unit that stores data of a plurality of mask images and data of a plurality of contrast images, each of the plurality of mask images being obtained by radiographing a subject to be examined in a different direction before contrast medium injection, each of the plurality of contrast images being obtained by radiographing the subject to be examined in a different direction after the contrast medium injection; a reconstruction unit that reconstructs first three-dimensional image data and second three-dimensional image data having a lower resolution than the first three-dimensional image data from the plurality of mask image data and reconstructs third three-dimensional image data and fourth three-dimensional image data having a lower resolution than the third three-dimensional image data from the plurality of contrast image data; a positional deviation amount calculating unit that calculates a positional deviation amount of the second three-dimensional image with respect to the fourth three-dimensional image; a positional deviation correcting unit that corrects the first three-dimensional image on the basis of the calculated positional deviation amount and creates fifth three-dimensional image data, and a processing unit that performs subtraction between the third three-dimensional image data and the fifth three-dimensional image data and creates sixth three-dimensional image data.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

Figure 1:
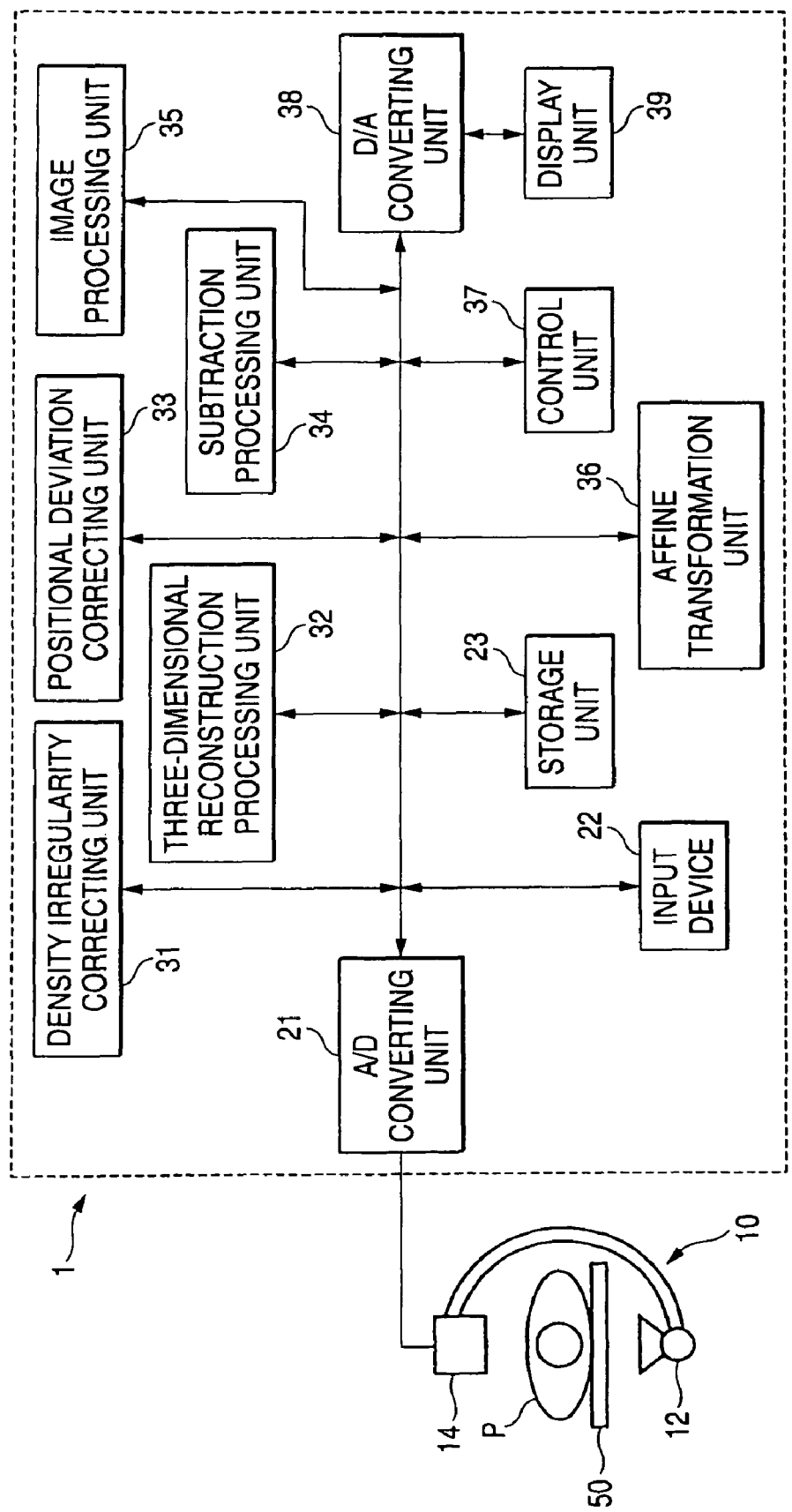
FIG. 1 is a diagram illustrating a structure of a three-dimensional image processing apparatus according to an embodiment of the invention.
Figure 2:
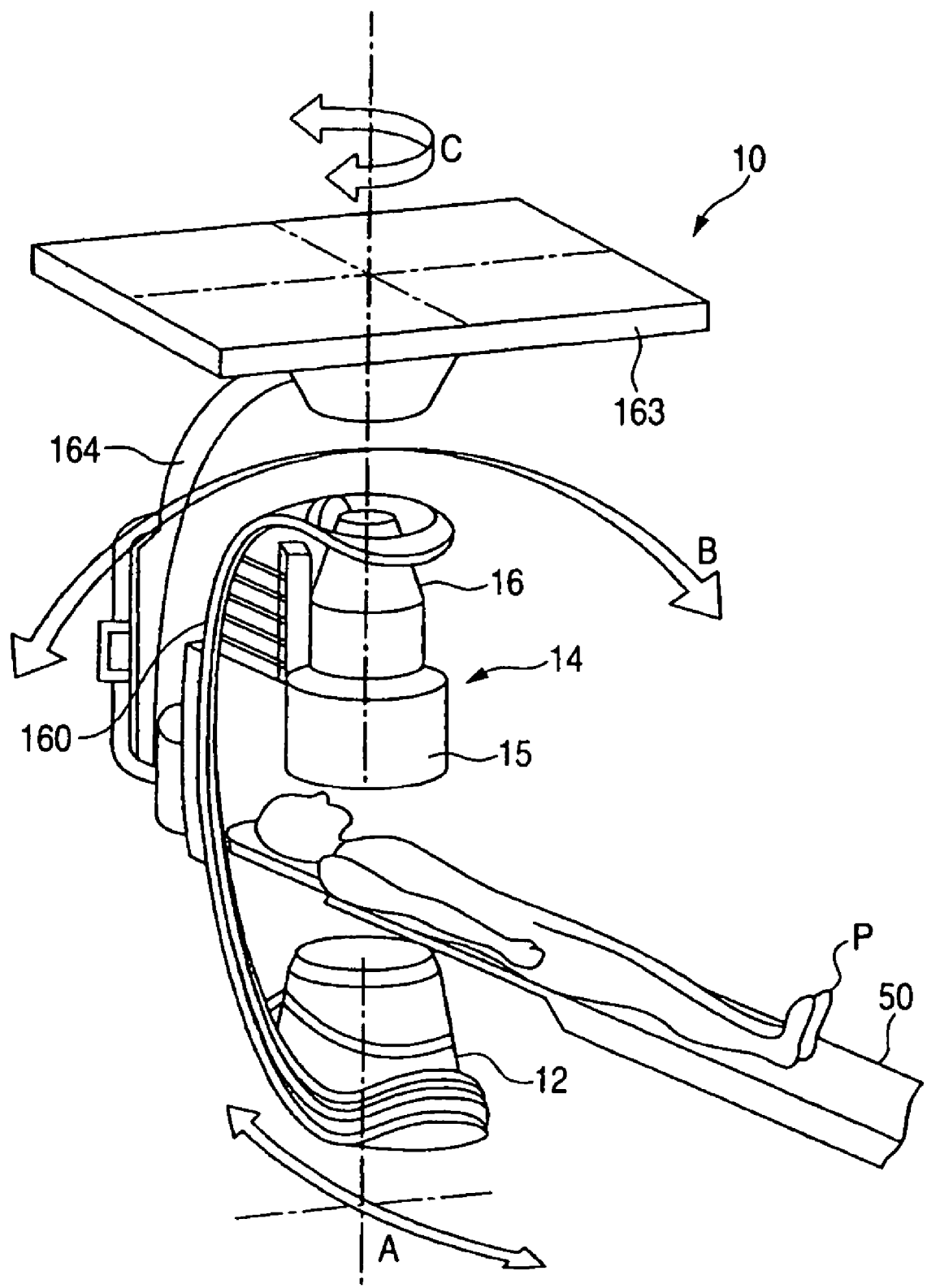
FIG. 2 is a diagram illustrating the exterior of an X-ray Angio apparatus of FIG. 1.

As shown in FIG. 1, an X-ray diagnosis apparatus has an X-ray Angio mechanism 10 and a three-dimensional image processing apparatus 1. The X-ray Angio mechanism 10 has an X-ray tube 12 and an X-ray detector 14, as shown in FIG. 2. The X-ray detector 14 has an image intensifier 15 and a TV camera 16. Further, the X-ray detector 14 is composed of a flat panel detector (FPD: flat X-ray detector) that has semiconductor detection elements disposed in a matrix. The X-ray tube 12 and the X-ray detector 14 are mounted on a C-type arm 160. A subject P to be examined is laid upon a top plate 50 of a bed and is positioned between the X-ray tube 12 and the X-ray detector 14. The C-type arm 160 is supported on a pillar 164 suspended from a ceiling base 163. The C-type arm 160 can rotate about three axes A, B, and C that are orthogonal to one another.

The three-dimensional image processing apparatus 1 includes a control unit 37, an A/D converting unit 21, an input device 22, a storage unit 23, a density irregularity correcting unit 31, a three-dimensional reconstruction processing unit 32, a positional deviation correcting unit 33, a subtraction processing unit 34, a three-dimensional image processing unit 35, an affine transformation unit 36, a D/A converting unit 38, and a display unit 39. The A/D converting unit 21 is connected to the X-ray detector 14, and the D/A converting unit 38 is connected to the display unit 39. The input device 22 has a keyboard and a mouse. The storage unit 23 stores various data, such as two-dimensional image data (mask image data and contrast image data), three-dimensional image data (volume data) or the like, which are input through the A/D converting unit 21. The density irregularity correcting unit 31 performs a process for correcting density irregularity depending on the apparatus with respect to the mask image data and the contrast image data. Specifically, image data, which is acquired in advance by radiographing a homogeneous phantom in the same radiography direction as in a case in which examination radiography is performed in a state in which there is no or the homogeneous phantom in a radiographic region between the X-ray tube 12 and the X-ray detector 14 and on which the density irregularity depending on the apparatus is reflected, is individually subtracted from each of the mask image data and the contrast image data of the subject, so that the density irregularity correction can be performed.

The three-dimensional reconstruction processing unit 32 has a distortion correction processing function for correcting image distortion, and a function for reconstructing data of a three-dimensional image (hereinafter, referred to as three-dimensional mask image) from data of a plurality of mask images each of which is obtained by radiographing the same subject in a different direction and reconstructing data of a three-dimensional image (hereinafter, referred to as three-dimensional contrast image) from data of a plurality of contrast images each of which is obtained by radiographing the same subject in a different direction. The distortion correcting function is performed only in a case in which the X-ray detector 14 constitutes the image intensifier, and does not need to be performed in a case in which the X-ray detector 14 is composed of the flat panel detector.

The positional deviation correcting unit 33 specifies the positional deviation between the three-dimensional contrast image and the three-dimensional mask image, that is, the positional deviation direction and distance between a position of the subject on the coordinate system of the three-dimensional contrast image and a position of the subject on the coordinate system of the three-dimensional mask image, and align a biogenic position and direction of the three-dimensional contrast image with a biogenic position and direction of the three-dimensional mask image in accordance with the specified positional deviation direction and distance. The subtraction processing unit 34 has a function for performing subtraction between the three-dimensional contrast image and the three-dimensional mask image two-dimensionally or three-dimensionally. The affine transformation unit 36 performs an enlargement process and a movement process on the image data. The image processing unit 35 creates display image data from the three-dimensional image data through surface rendering processing.

Figure 3:
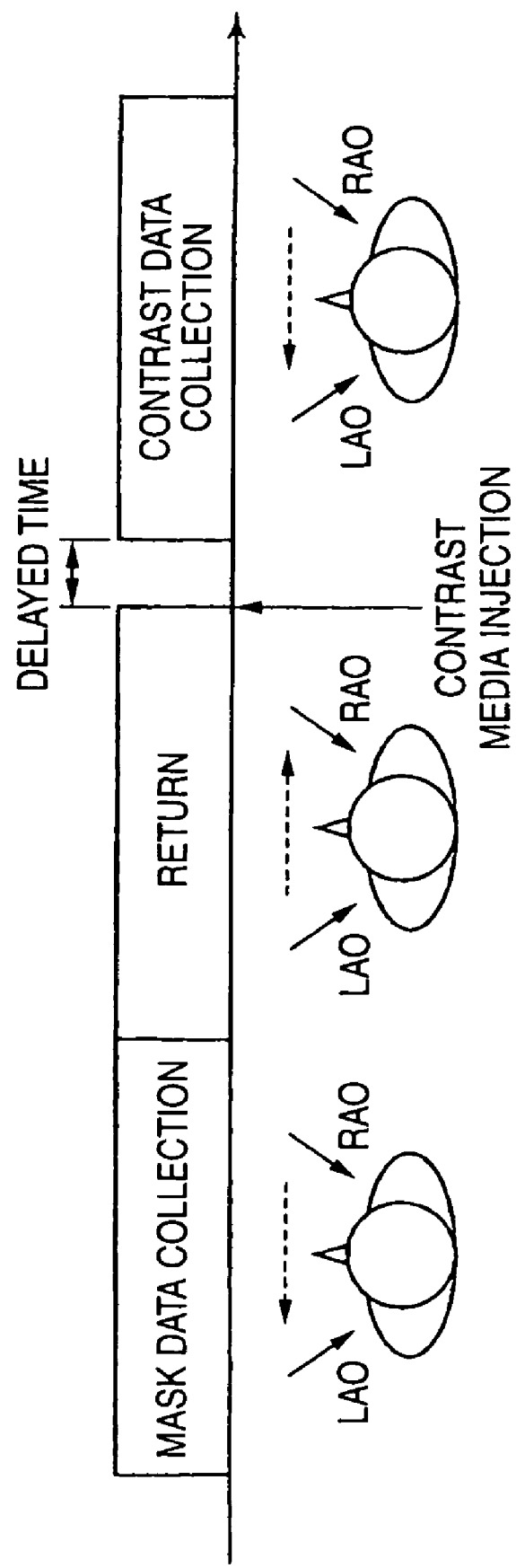
FIG. 3 is a diagram schematically illustrating a radiographed sequence according to the embodiment.

Next, the operation of the present embodiment will be described. The C-type arm 160 can rotate at a high speed like a propeller by means of a motor. Therefore, the C-type arm 160 can rotate for a short amount of time at an angle of one hundred and eighty degrees or more around the subject. As shown in FIG. 3, the radiography is repeatedly performed at one-degree interval while rotating the arm 160 and varying a radiography direction from an RAO direction (first oblique direction) to an LAO direction (second oblique direction), so that data of two hundred sheets of projection images obtained when the rotational angle becomes two hundred degrees is collected. The data of the two hundred sheets of mask images, which has been collected, is converted into a digital signal by the A/D converting unit 21 and is then stored in the storage unit 23. The collection of the image data is performed twice before contrast medium injection and after contrast medium injection. Before the contrast medium is injected, data of two hundred sheets of mask images is collected and is then stored in the storage unit 23. The radiography direction returns from the LAO direction (second oblique direction) to the RAO direction (first oblique direction). After the contrast medium is injected, if the proper delayed time according to a corresponding radiography part passes, the radiography is repeatedly performed under the same conditions. As a result, data of two hundred sheets of projection images (contrast images) is collected and is then stored in the storage unit 23.

After the radiography is completed, an image process can be started at any time in order to create a three-dimensional blood vessel image. In the image processing apparatus according to the present embodiment, there are two kinds of image processing modes. An operator can create the three-dimensional blood vessel image using any one of the two kinds of image processing modes. One of the two kinds of image processing modes is the same as that of the related art. Specifically, the mask images and the contrast images of same direction are subtracted, the three-dimensional reconstruction process is performed on the obtained two hundred sheets of subtraction images, and the three-dimensional blood vessel images are created. The other mode is a newly devised mode. Specifically, the three-dimensional images (three-dimensional mask images) are reconstructed from the two hundred sheets of mask images whose radiography directions are different from one another. In the same manner, the three-dimensional images (three-dimensional contrast images) are reconstructed from the two hundred sheets of contrast images whose radiography directions are different from one another. In addition, after correcting the positional deviation between the three-dimensional mask images and the three-dimensional contrast images, the three-dimensional mask images and the three-dimensional contrast images are subtracted, so that the three-dimensional blood vessel images are created. When a patient moves right after being injected with the contrast medium, the movement of the patient is not the two-dimensional movement. Therefore, in the two-dimensional correction like the pixel shift, it is not possible to suppress the corresponding artifacts. In the present embodiment, the three-dimensional movement of the patient is detected in the three-dimensional space and the three-dimensional correction is carried out. Therefore, it is possible to effectively suppress the artifact. Hereinafter, the newly devised image process mode will be described.

Figure 4:
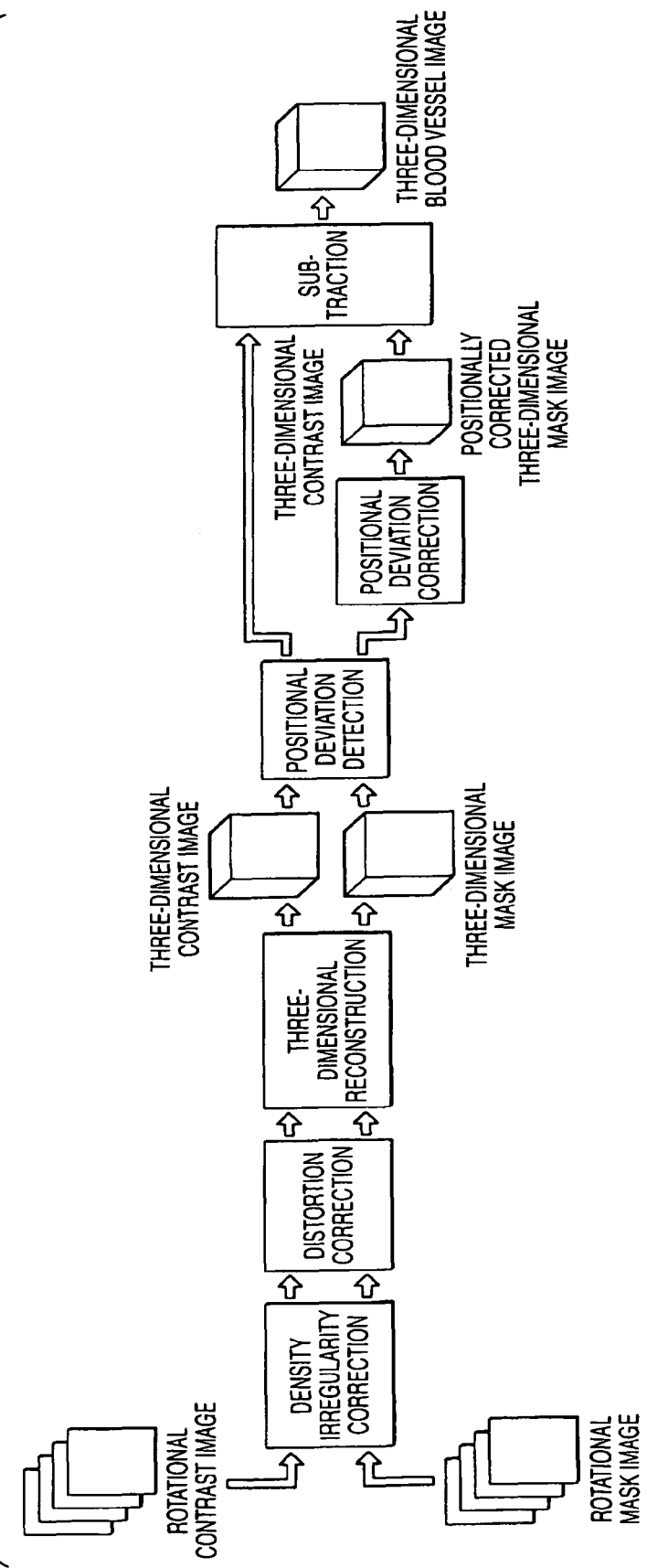
FIG. 4 is a diagram illustrating a sequence of a three-dimensional blood vessel image creating process by the three-dimensional image processing apparatus of FIG. 1.
Figure 5:
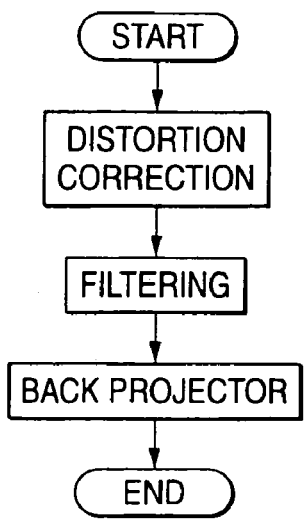
FIG. 5 is a diagram illustrating a process sequence of a three-dimensional reconstruction processing unit of FIG. 1.
Figure 6A:
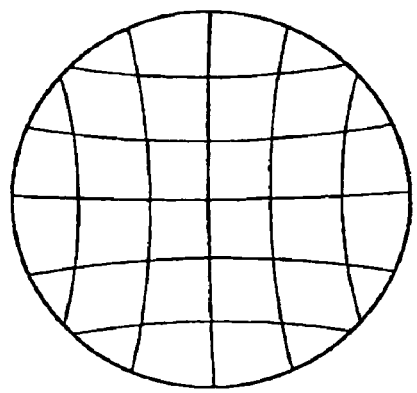
FIGS. 6a and 6b are diagrams complementarily illustrating a distortion correcting process of FIG. 5.
Figure 6B:
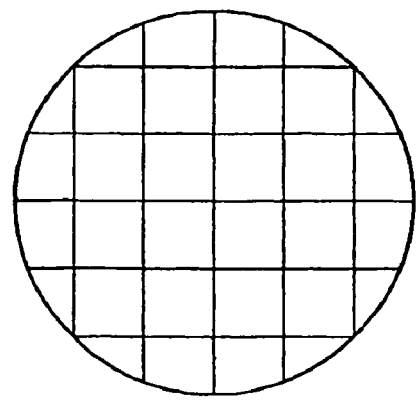

As shown in FIG. 4, first, in the density irregularity correcting unit 31, the density irregularity is corrected for each of the mask images and the contrast images. Next, as shown in FIG. 5, the distortion correction is performed in the three-dimensional reconstruction processing unit 32. For the simplification of description, it is assumed that a phantom is formed by disposing wires in a square lattice at equal intervals in vertical and horizontal directions. If the phantom is radiographed in a state in which it is placed on a front surface of the image intensifier 15 of the X-ray detector 14, a projection image of the square lattice is preferably obtained, as shown in FIG. 6B. However, actually, as shown in FIG. 6A, the distortion occurs by the influence of the pin cushion distortion due to the shape of the front surface of the image intensifier 15 or the S-shaped distortion due to the geomagnetism. Accordingly, the image data of FIG. 6A is collected in advance, and intersections between wires are extracted from the collected image data as lattice points. Since the lattice points are disposed at the same interval when the distortion does not occur, the lattice points are made to be disposed at the same interval so as to correct the distortion. Further, points other than the lattice points are corrected by using data of the peripheral lattice points. Furthermore, since the distortion distribution is different for every angle, a distortion distribution table, which is measured from the collected phantom projection images for every angle, is stored, and the distortion is corrected on the basis of the distortion distribution table. In addition, when the X-ray detector 14 is composed of the FPD, the distortion correction does not need to be performed.

Next, the three-dimensional reconstruction process is executed in the three-dimensional reconstruction processing unit 32. As an example of a reconstruction method, in the present embodiment, a filtered back projection method suggested by Feldkamp et al. is used. As shown in FIG. 5, the filtering through a proper convolution filter like, for example, Shepp & Logan or Ramachandran is performed on the two hundred sheets of images each of which is obtained by radiographing the same subject in a different direction. Next, the back projection is performed, so that the three-dimensional image is reconstructed. In this case, the reconstruction region is defined as an inscribed cylinder with respect to X-ray beams in all directions of the X-ray tube 12. The inside of the cylinder is three-dimensionally discretized by the length d at the central portion of the reconstruction region projected onto the width of the one detection element of the X-ray detector 14, and the reconstruction image of the discrete point data needs to be obtained. In this case, an example of the discrete interval is illustrated, but the discrete interval may be different for each of the apparatuses or makers. Accordingly, the discrete interval defined by the apparatus may be basically used.

The three-dimensional mask image data and the three-dimensional contrast image data, which have been reconstructed, are transmitted from the storage unit 23 to the image processing unit 35, and are displayed three-dimensionally by the volume rendering method or the like. In this case, the displayed three-dimensional image is a three-dimensional image that includes original information, such as a blood vessel, a bone, soft tissue or the like.

Figure 7A:
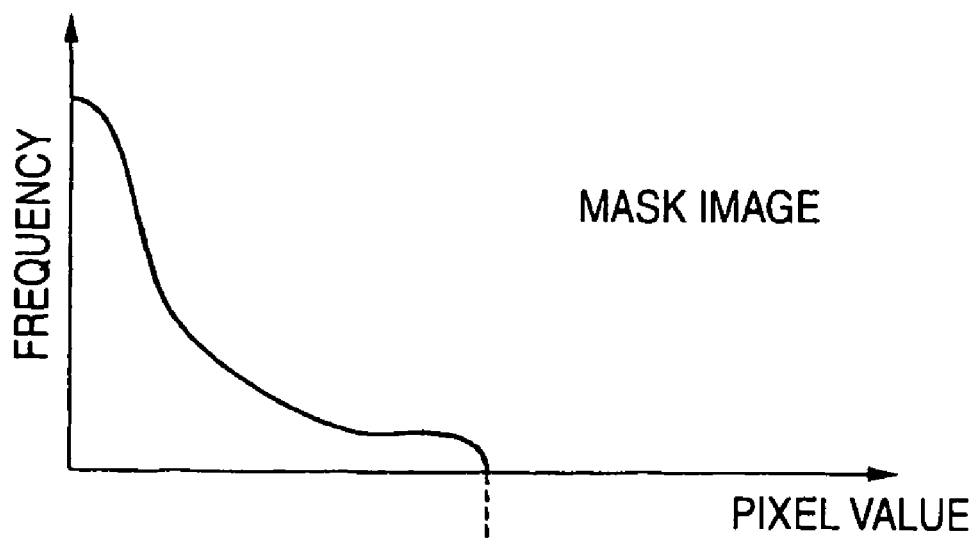
FIGS. 7a and 7b are diagrams complementarily illustrating the pre-processing of positional deviation detection of FIG. 4.
Figure 7B:
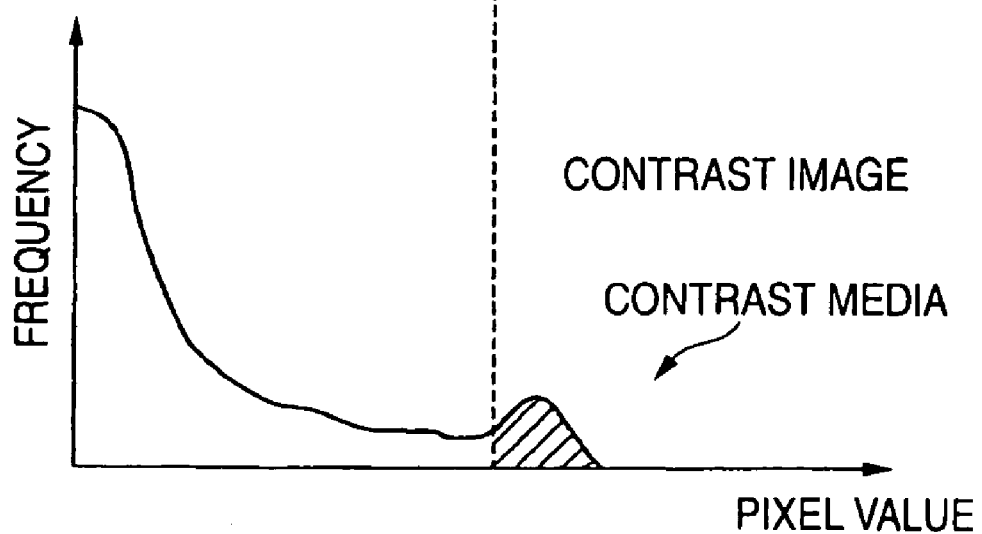
Figure 8A:
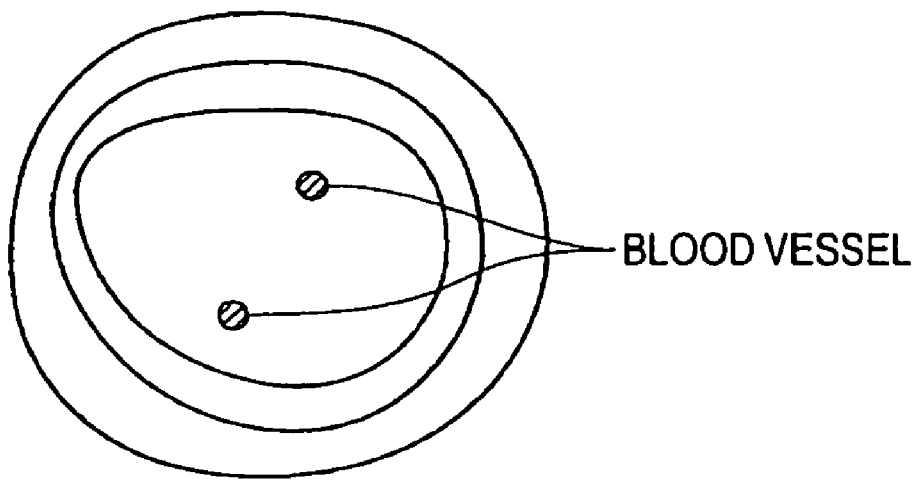
FIGS. 8a and 8b are diagrams complementarily illustrating the pre-processing of positional deviation detection of FIG. 4.
Figure 8B:
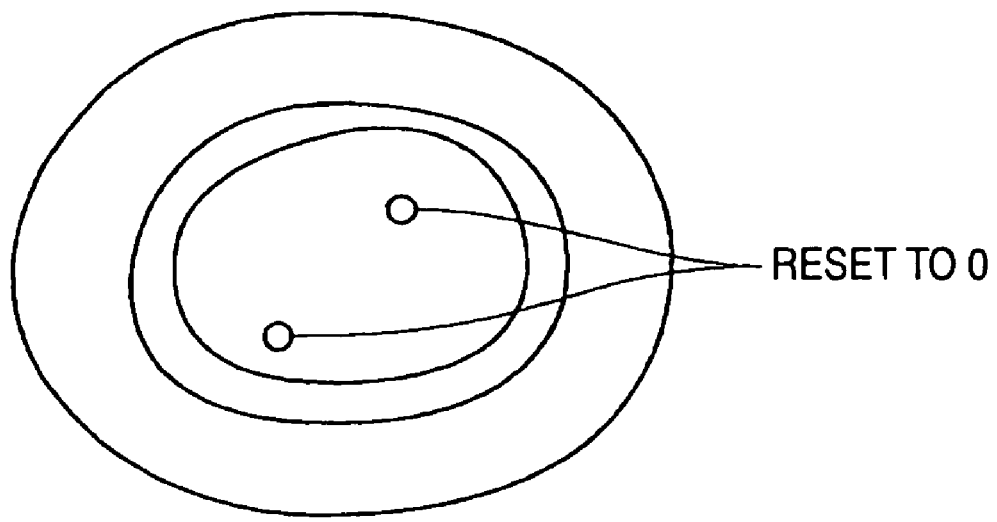

Next, a process for correcting the positional deviation between the three-dimensional mask image and the three-dimensional contrast image and aligning the positions is executed by the positional deviation correcting unit 33. As the preprocess for the positional deviation correction, a density transformation process is executed in the positional deviation correcting unit 33. In the positional deviation correction unit 33, a histogram of the pixel value of the three-dimensional mask image (FIG. 7A) and a histogram of the pixel value of the three-dimensional contrast image (FIG. 7B) are created and are then compared with each other. The histogram of the pixel value of the three-dimensional mask image is subtracted from the histogram of the pixel value of the three-dimensional contrast image, so that a portion corresponding to the contrast medium (oblique portion of FIG. 7B) is extracted. Actually, in order to remove the influence of the noise, a portion, which has a predetermined frequency or more and is continuous on an axis of the pixel value, is specified as a portion corresponding to the contrast medium. A minimum value of the portion corresponding to the contrast medium (or maximum value) is determined as a threshold value that discriminates between the region where the contrast medium is distributed and the other region. As shown in FIGS. 8A and 8B, with respect to the pixels of the three-dimensional contrast image having a larger pixel value (or a smaller pixel value) than the corresponding threshold value, the corresponding pixel values are substituted by zero.

After the preprocess, the positional deviation detection is performed. The positional deviation between the three-dimensional contrast image and the three-dimensional mask image is specified. The positional deviation of the three-dimensional mask image with respect to the three-dimensional contrast image is typically specified. However, the positional deviation of the three-dimensional contrast image with respect to the three-dimensional mask image may be specified, and the positional deviation of the three-dimensional contrast image with respect to a reference position and the positional deviation of the three-dimensional mask image with respect to the same reference position may be specified. In the present embodiment, the specifying of the positional deviation of the three-dimensional mask image with respect to the three-dimensional contrast image will be described. In the specifying of the positional deviation, the deviated distance and rotational angle is specified with respect to each of the axes of XYZ between the subject position of the three-dimensional contrast image on the coordinate system and the subject position of the three-dimensional mask image on the coordinate system.

According to a positional deviation detecting method, a correlation coefficient between the three-dimensional contrast image and the three-dimensional mask image is calculated, and the calculation process of the correlation coefficient is repeated while moving interval-by-interval the position of the three-dimensional mask image with respect to the three-dimensional contrast image with respect to three axes of XYZ. As a result, the position having the lowest correlation coefficient is determined as the corresponding position, and a movement vector with respect to the corresponding position is stored. Here, the correlation operation can be represented as the following equation.

$$CR(\Delta x, \Delta y, \Delta z) = \frac{1}{T} \sum_{z=0}^{N-1} \sum_{Y=0}^{N-1} \sum_{x=0}^{N-1} \{D[f_1(x+\Delta x, y+\Delta y, z+\Delta z) - f_2(x, y, z)]\}^2$$ [Equation 1]

In this case, D (f1-f2) can be represented as the following equation.

$$D(f1 - f2) = \begin{cases} 0 & : f1 \text{ or } f2 \text{ is zero} \\ 0 & : f1 \text{ or } f2 \text{ indicates the region other than the reconstruction region} \\ f1 - f2 & : \end{cases}$$ [Equation 2]

In this case, f1 or f2 is zero, and f1 or f2 indicates the region other than the reconstruction region.

Further, a reference character T indicates the number of voxels on which the correlation operation is performed. If all of the voxels are subjects of the correlation operation, T satisfies the condition $T=N^3$. However, the subjects of the correlation operation are voxels of the blood vessel or are regions of which parts protrude from the reconstruction regions, they are excluded from the operation subjects in the function D. Therefore, T satisfies the condition $T<N^3$. Here, f1 (x+$\Delta$x, y+$\Delta$y, z+$\Delta$z) corresponds to the three-dimensional mask image, and f2 (x, y, z) corresponds to the three-dimensional contrast image. A reference character N indicates a size of the voxel matrix of each of the three-dimensional mask image and the three-dimensional contrast image, and ($\Delta$x, $\Delta$y, $\Delta$z) indicates a shift vector. CR ($\Delta$x, $\Delta$y, $\Delta$z) is a result of the correlation operation, and the correlation operation result is calculated while shifting each of the $\Delta$x, $\Delta$y, and $\Delta$z within a range of $-\Delta$ to $+\Delta$, and a shift vector where the calculated result becomes the minimum is detected as positional deviation. In addition, the representation can not be given in the above-mentioned equations, but when the correlation operation is performed, the operation is skipped with respect to a region other than a partial region of the three-dimensional contrast image set to zero at the preprocess for the positional deviation correction f2 (x, y, z)=0. The range of the correlation operation is between $-\Delta$ to $+\Delta$, and the step of the operation (step of each of $\Delta$x, $\Delta$y, and $\Delta$z) is performed for every $\delta$. Further, only the shift is represented in the above-mentioned equations, but it is necessary that the angle deviation be detected by introducing the rotational angles $\Delta\theta$x, $\Delta\theta$y, and $\Delta\theta$z. Each of the $\Delta\theta$x, $\Delta\theta$y, and $\Delta\theta$z indicates the rotational angle about each of an X axis, a Y axis, and a Z axis. The correlation operation is performed while varying each of the rotational angles $\Delta\theta$x, $\Delta\theta$y, and $\Delta\theta$z within a range between $-\theta$ to $+\theta$ for every $\Delta\theta$, such that the deviation amount becoming the minimum value is calculated. In addition, since an equation where the angle variation is introduced becomes very complicated, the angle variation introduction will be omitted in the present embodiment.

Further, although the correlation coefficient is calculated using all of the image data, in order to reduce the calculated amount, the calculation of the correlation coefficient may be limited to the partial region constituting a portion of the entire region of the three-dimensional image and the deviated amount may be calculated. The partial region is set to a non-contrast region so as to improve the deviated amount calculation precision by excluding the contrast effect. In the non-contrast region, a bone structure is typically selected as an anatomical structure. When a head is examined, a skull base structure is preferably selected as the partial region. The skull base structure can be relatively easily extracted by performing the threshold value process corresponding to the bone with respect to the searching range including the skull base portion limited by the operator.

In addition, the correlation coefficient is calculated using all of the image data, but in order to reduce the calculated amount, the correlation operation may first be performed by using the reduced image having a small-sized voxel matrix, and the shift amount may be calculated while gradually returning to the size of the original image. For example, if N satisfies the condition N=512, each size of the three-dimensional mask image and the three-dimensional contrast image each having a size of 512 is first reduced to a size of $32^3$, and the operation is performed between the three-dimensional mask image having a size of $32^3$ and the three-dimensional contrast image having a size of $32^3$. After the operation is performed between the three-dimensional mask image having a size of $32^3$ and the three-dimensional contrast image having a size of $32^3$, the operation is performed between the three-dimensional mask image having a size of $64^3$ and the three-dimensional contrast image having a size of $64^3$. At this time, the operation starts by using the result obtained by performing the operation between the three-dimensional mask image having a size of $32^3$ and the three-dimensional contrast image having a size of $32^3$ as an initial value of the operation between the three-dimensional mask image having a size of $64^3$ and the three-dimensional contrast image having a size of $64^3$. Specifically, for example, it is assumed that according to the result of the operation between the three-dimensional mask image having a size of $32^3$ and the three-dimensional contrast image having a size of $32^3$, the value of the correlation operation becomes the minimum in a state in which the three-dimensional mask image rotates at each of rotational angles ($\Delta\theta x$, $\Delta\theta y$, and $\Delta\theta z$), and then ($\Delta x$, $\Delta y$, and $\Delta z$) are shifted. When the operation starts between the three-dimensional mask image having a size of $64^3$ and the three-dimensional contrast image having a size of $64^3$, the correlation operation starts in a state in which the three-dimensional mask image rotates at each of the angles ($\Delta\theta x$, $\Delta\theta y$, and $\Delta\theta z$), and then ($\Delta x$, $\Delta y$, and $\Delta z$) are shifted. After that, the operation is repeated while sequentially increasing the size of the voxel matrix in the order of $64^3$, $128^3$, $256^3$, and $512^3$ so as to gradually increase the resolution, so that the positional deviation amount is calculated. According to this method, the operation amount can be markedly reduced. In addition, a macroscopic search is initially performed and a microscopic search is gradually performed. Accordingly, it can be prevented that the correlation coefficient is trapped in not an optimal solution but a semi-optimal solution.

Next, the positional correction is performed. If it is assumed that the positional deviation specified in the positional deviation detecting process is ($\Delta\theta x0$, $\Delta\theta y0$, and $\Delta\theta z0$) and ($\Delta x0$, $\Delta y0$, and $\Delta z0$), the three-dimensional image rotates at each of the angles of ($\Delta\theta x0$, $\Delta\theta y0$, and $\Delta\theta z0$), and ($\Delta x0$, $\Delta y0$, and $\Delta z0$) are then shifted. As a result, the three-dimensional mask image, in which the positional deviation is corrected, is created.

Next, the subtraction process is performed. The subtraction processing unit 34 subtracts the three-dimensional mask image in which positional deviation is corrected from the three-dimensional contrast image. Thereby, the three-dimensional blood vessel image is created. The data of the created three-dimensional blood vessel image is transmitted to the three-dimensional image processing unit 35. After that, the volume rendering process or the like is performed on the data of the created three-dimensional blood vessel image so as to be displayed on a screen.

In the above-mentioned description, the positional deviation correction is performed with respect to the three-dimensional mask image, but may be performed with respect to the three-dimensional contrast image.

In addition, in the above-mentioned description, the operator selects the process mode, but the system may determine the corresponding process mode automatically. The determination is performed as follows. It is checked whether the subtraction image between the two-dimensional mask image and the two-dimensional contrast image is a signal having a predetermined magnitude which is opposite to the signal of the contrast medium in a direction for each of the pixels from a first frame to an N-th frame (assuming that N frames are collected). If the signal of the contrast medium is negative, the pixels having the pixel value equal to or greater than the threshold value Th are determined as artifacts. The total sum of the pixel values of the artifacts is calculated, and if the total sum is greater than a predetermined value, it is determined that the patient has moved, and the reconstruction accompanied with the movement correction is performed. If the total sum is equal to or smaller than the predetermined value, the construction that is not accompanied with the movement correction is performed. The example where the total sum of the pixel values are calculated has been described, but the number of pixels determined as the artifacts is calculated, and if the number of the pixels is greater than the predetermined value, it is determined that the patient has moved, and the reconstruction accompanied with the movement correction may be performed. If the total sum is equal to or smaller than the predetermined value, the construction that is not accompanied with the movement correction may be performed.

Figure 9:
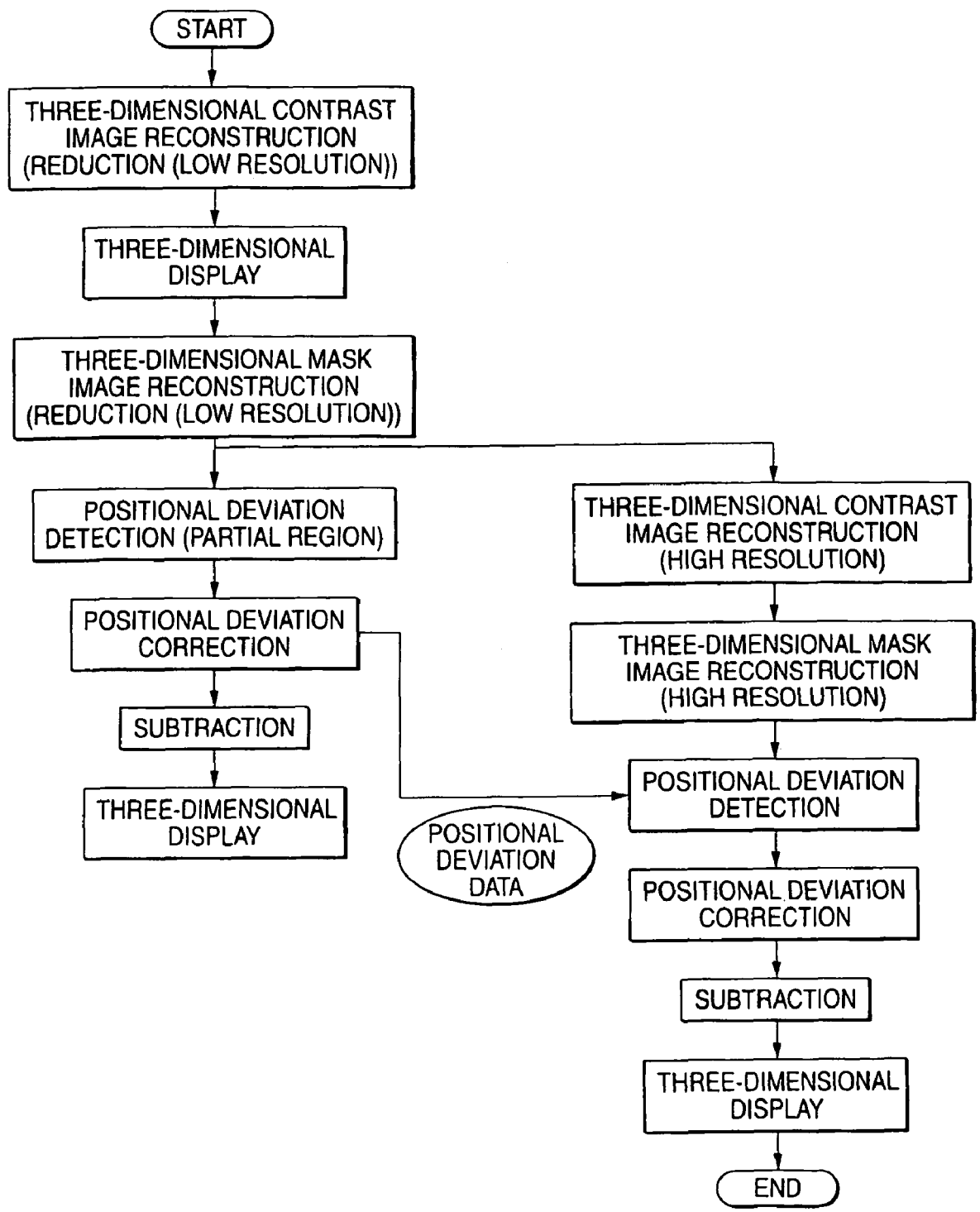
FIG. 9 is a flowchart illustrating another process sequence according to a modification of the embodiment.
Figure 10:
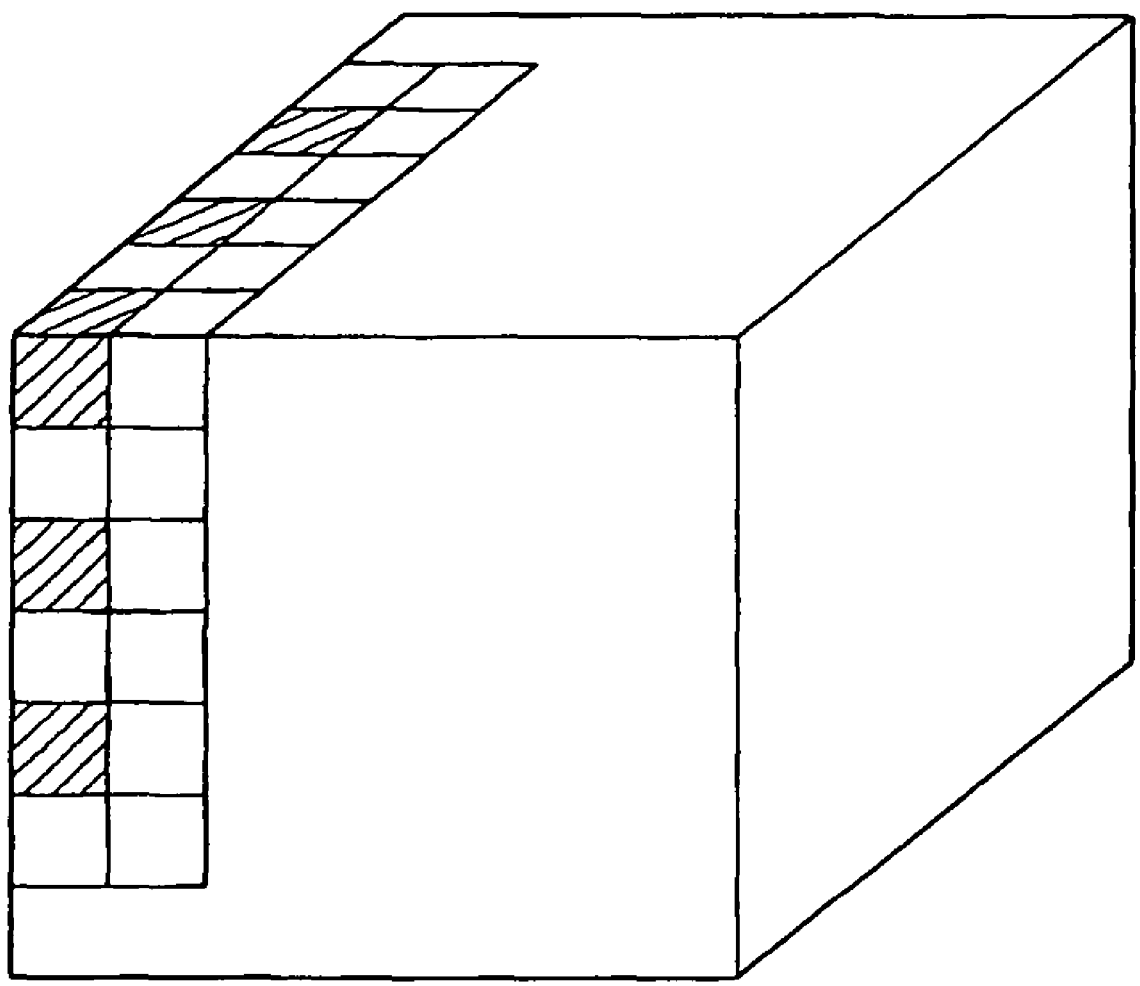
FIG. 10 is a diagram complementarily illustrating an image reconstruction process (reduction) of FIG. 9.

In addition, all of the steps have been processed according to a schedule, but a parallel process is executed with respect to all of the steps, so that all of the steps can be executed at a high speed. As shown in FIG. 9, specifically, as a first step, a three-dimensional contrast image is reconstructed. At this time, the reconstruction image is reconstructed as a reduction image such that it has not a voxel matrix size of $512^3$ but a voxel matrix size of $256^3$. This is a reconstruction method in which the entire region having the size of $512^3$ is reduced so as to have the size of $256^3$. According to this method, first, the size of the projection data may be reduced from the size of $512^2$ to the size of $256^2$, and the reconstruction may be performed. Even though the projection data is maintained as it is and voxels are reconstructed so as to be skipped one-by-one at the time of the reconstruction operation as shown in FIG. 10, the central values of adjacent eight voxels may be calculated as representative values. In a second step, the three-dimensional contrast image as the reduction image is displayed three-dimensionally by a volume rendering method or the like. In this case, the displayed three-dimensional image has information, such as a blood vessel, a bone, soft tissue or the like. In a third step, the three-dimensional mask image is reconstructed as the reduced image. At this time, the reconstruction image is reconstructed so as to have a size of $256^3$. In a fourth step, the positional deviation between the three-dimensional mask image as the reduction image and the three-dimensional contrast image is detected. In a fifth step, the three-dimensional mask image and the three-dimensional contrast image are reconstructed so as to have the full size of $512^3$ while executing the fourth step. In a sixth step, the positional deviation of the three-dimensional mask image of the full size is corrected in accordance with the shift and the rotational angle determined by detecting the positional deviation, the subtraction is performed between the three-dimensional mask image and the three-dimensional contrast image, and the three-dimensional blood vessel image is created. The three-dimensional blood vessel image is displayed three-dimensionally by the volume rendering method or the like.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concepts as defined by the appended claims and their equivalents.

What is claimed is:

1. A three-dimensional image processing apparatus comprising:
   a storage unit that stores data of a plurality of mask images and data of a plurality of contrast images, each of the plurality of mask images being obtained by radiographing a subject to be examined with radiation incident on the subject from different respective directions before contrast medium injection, each of the plurality of contrast images being obtained by radiographing the subject to be examined in respective different radiation incident directions after the contrast medium injection;

a reconstruction unit that reconstructs first three-dimensional image data from the plurality of mask image data and reconstructs second three-dimensional image data from the plurality of contrast image data;

a positional deviation correcting unit that corrects positional deviation of the first three-dimensional image with respect to the second three-dimensional image on the basis of the comparison result between an anatomical structure in a partial region of the first three-dimensional image data and an anatomical structure in a corresponding partial region of the second three-dimensional image data, and creates third three-dimensional image data, including an extraction unit which extracts the partial regions of the first and second three-dimensional image data using a threshold related to bone; and a processing unit that performs subtraction between the second three-dimensional image data and the third three-dimensional data and creates fourth three-dimensional image data.

2. A three-dimensional image processing apparatus comprising:

a storage unit that stores data of a plurality of mask images and data of a plurality of contrast images, each of the plurality of mask images being obtained by radiographing a subject to be examined with radiation incident on the subject from different respective directions before contrast medium injection, each of the plurality of contrast images being obtained by radiographing the subject to be examined in respective different radiation incident directions after the contrast medium injection;

a reconstruction unit that reconstructs first three-dimensional image data from the plurality of mask image data and reconstructs second three-dimensional image data from the plurality of contrast image data;

a positional deviation correcting unit that corrects positional deviation of the second three-dimensional image with respect to the first three-dimensional image on the basis of the comparison result between an anatomical structure in a partial region of the first three-dimensional image data and an anatomical structure in a corresponding partial region of the second three-dimensional image data, and creates third three-dimensional image data, including an extraction unit which extracts the partial regions of the first and second three-dimensional image data using a threshold related to bone; and a processing unit that performs subtraction between the third three-dimensional image data and the first three-dimensional image data and creates fourth three-dimensional image data.

3. The three-dimensional image processing apparatus according to claim 1, wherein the positional deviation correcting unit is limited to a partial region in a correction range, and specifies positional deviation between the second three-dimensional image and the first three-dimensional image.

4. The three-dimensional image processing apparatus according to claim 3, wherein the partial region is a non-contrast region.

5. The three-dimensional image processing apparatus according to claim 1, wherein the anatomical structure is a bone structure.

6. The three-dimensional image processing apparatus according to claim 5, wherein the anatomical structure is a skull base structure.

7. The three-dimensional image processing apparatus according to claim 1, wherein the positional deviation correcting unit specifies positional deviation of the first three-dimensional image with respect to the second three-dimensional image while shifting and/or rotating the first three-dimensional image with respect to the second three-dimensional image by a predetermined amount.

8. A three-dimensional image processing apparatus comprising:

a storage unit that stores data of a plurality of mask images and data of a plurality of contrast images, each of the plurality of mask images being obtained by radiographing a subject to be examined with radiation incident on the subject from different respective directions before contrast medium injection, each of the plurality of contrast images being obtained by radiographing the subject to be examined in respective different radiation incident directions after the contrast medium injection;

a reconstruction unit that reconstructs first three-dimensional image data from the plurality of mask image data and reconstructs second three-dimensional image data from the plurality of contrast image data;

a positional deviation amount calculating unit that calculates a positional deviation amount of the first three-dimensional image with respect to the second three-dimensional image on the basis of the comparison result between a partial region of the first three-dimensional image data and a corresponding partial region of the second three-dimensional image data, including an extraction unit which extracts the partial regions of the first and second three-dimensional image data using a threshold related to bone;

a positional deviation correcting unit that corrects the first three-dimensional image on the basis of the calculated positional deviation amount and creates third three-dimensional image data, and a processing unit that performs subtraction between the second three-dimensional image data and the third three-dimensional image data and creates fourth three-dimensional image data.

9. A three-dimensional image processing apparatus comprising:

a storage unit that stores data of a plurality of mask images and data of a plurality of contrast images, each of the plurality of mask images being obtained by radiographing a subject to be examined with radiation incident on the subject from different respective directions before contrast medium injection, each of the plurality of contrast images being obtained by radiographing the subject to be examined in respective different radiation incident directions after the contrast medium injection;

a reconstruction unit that reconstructs first three-dimensional image data from the plurality of mask image data and reconstructs second three-dimensional image data from the plurality of contrast image data;

a positional deviation amount calculating unit that calculates a positional deviation amount of the second three-dimensional image with respect to the first three-dimensional image on the basis of the comparison result between a partial region of the first three-dimensional image data and a corresponding partial region of the second three-dimensional image data, including an extraction unit which extracts the partial regions of the first and second three-dimensional image data using a threshold related to bone;

a positional deviation correcting unit that corrects the second three-dimensional image data on the basis of the calculated positional deviation amount and creates third three-dimensional image data, and a processing unit that performs subtraction between the third three-dimensional image data and the first three-dimensional image data and creates fourth three-dimensional image data.

10. The three-dimensional image processing apparatus according to claim 8,
wherein the partial region is a non-contrast region.

11. The three-dimensional image processing apparatus according to claim 10,
wherein the non-contrast region is a bone structure.

12. The three-dimensional image processing apparatus according to claim 11
wherein the bone structure is a skull base structure.

13. The three-dimensional image processing apparatus according to claim 8,
wherein the positional deviation correcting unit specifies positional deviation of the first three-dimensional image with respect to the second three-dimensional image while shifting and/or rotating the first three-dimensional image with respect to the second three-dimensional image by a predetermined amount.

14. A three-dimensional image processing apparatus comprising:

a storage unit that stores data of a plurality of mask images and data of a plurality of contrast images, each of the plurality of mask images being obtained by radiographing a subject to be examined with radiation incident on the subject from different respective directions before contrast medium injection, each of the plurality of contrast images being obtained by radiographing the subject to be examined in respective different radiation incident directions after the contrast medium injection;

a reconstruction unit that reconstructs first three-dimensional image data and second three-dimensional image data having a lower resolution than the first three-dimensional image data from the plurality of mask image data and reconstructs third three-dimensional image data and fourth three-dimensional image data having a lower resolution than the third three-dimensional image data from the plurality of contrast image data;

a positional deviation amount calculating unit that calculates a positional deviation amount of the second three-dimensional image with respect to the fourth three-dimensional image in a partial region of the second three-dimensional image and a corresponding partial region of the fourth three-dimensional image, including an extraction unit which extracts the partial regions of the first and second three-dimensional image data using a threshold related to bone;

a positional deviation correcting unit that corrects the first three-dimensional image on the basis of the calculated positional deviation amount and creates fifth three-dimensional image data, and a processing unit that performs subtraction between the third three-dimensional image data and the fifth three-dimensional image data and creates sixth three-dimensional image data.

15. A three-dimensional image processing apparatus comprising:

a storage unit that stores data of a plurality of mask images and data of a plurality of contrast images, each of the plurality of mask images being obtained by radiographing a subject to be examined with radiation incident on the subject from different respective directions before contrast medium injection, each of the plurality of contrast images being obtained by radiographing the subject to be examined in respective different radiation incident directions after the contrast medium injection;

a reconstruction unit that reconstructs first three-dimensional image data and second three-dimensional image data having a lower resolution than the first three-dimensional image data from the plurality of mask image data and reconstructs third three-dimensional image data and fourth three-dimensional image data having a lower resolution than the third three-dimensional image data from the plurality of contrast image data;

a positional deviation amount calculating unit that calculates a positional deviation amount of the fourth three-dimensional image with respect to the second three-dimensional image in a partial region of the fourth three-dimensional image and a corresponding partial region of the second three-dimensional image, including an extraction unit which extracts the partial regions of the first and second three-dimensional image data using a threshold related to bone;

a positional deviation correcting unit that corrects the third three-dimensional image on the basis of the calculated positional deviation amount and creates fifth three-dimensional image data, and a processing unit that performs subtraction between the fifth three-dimensional image data and the first three-dimensional image data and creates sixth three-dimensional image data.

16. A three-dimensional image processing apparatus comprising:

a storage unit that stores data of a plurality of mask images and data of a plurality of contrast images, each of the plurality of mask images being obtained by radiographing a subject to be examined with radiation incident on the subject from different respective directions before contrast medium injection, each of the plurality of contrast images being obtained by radiographing the subject to be examined in respective directions different radiation incident directions after the contrast medium injection;

a reconstruction unit that reconstructs first three-dimensional image data and second three-dimensional image data having a lower resolution than the first three-dimensional image data from the plurality of mask image data and reconstructs third three-dimensional image data and fourth three-dimensional image data having a lower resolution than the third three-dimensional image data from the plurality of contrast image data;

a first positional deviation amount calculating unit that calculates a first positional deviation amount of the second three-dimensional image with respect to the fourth three-dimensional image in a corresponding partial region of the second three-dimensional image and a partial region of the fourth three-dimensional image;

a second positional deviation amount calculating unit that calculates a second positional deviation amount of the first three-dimensional image with respect to the third three-dimensional image in a partial region of the first three-dimensional image and a corresponding partial region of the third three-dimensional image using the calculated first positional deviation amount;

an extraction unit which extracts the partial regions of the first, second, third and fourth three-dimensional image data using a threshold related to bone;

a positional deviation correcting unit that corrects the first three-dimensional image on the basis of the calculated second positional deviation amount and creates fifth three-dimensional image data, and a processing unit that performs subtraction between the third three-dimensional image data and the fifth three-dimensional image data and creates sixth three-dimensional image data.

17. A three-dimensional image processing apparatus comprising:

a storage unit that stores data of a plurality of mask images and data of a plurality of contrast images, each of the plurality of mask images being obtained by radiographing a subject to be examined with radiation incident on the subject from different respective directions before contrast medium injection, each of the plurality of contrast images being obtained by radiographing the subject to be examined in respective different radiation incident directions after the contrast medium injection;

a reconstruction unit that reconstructs first three-dimensional image data and second three-dimensional image data having a lower resolution than the first three-dimensional image data from the plurality of mask image data and reconstructs third three-dimensional image data and fourth three-dimensional image data having a lower resolution than the third three-dimensional image data from the plurality of contrast image data;

a first positional deviation amount calculating unit that calculates a first positional deviation amount of the fourth three-dimensional image with respect to the second three-dimensional image in a partial region of the fourth three-dimensional image and a corresponding partial region of the second three-dimensional image;

a second positional deviation amount calculating unit that calculates a second positional deviation amount of the third three-dimensional image with respect to the first three-dimensional image in a partial region of the third three-dimensional image and a corresponding partial region of the first three-dimensional image using the calculated first positional deviation amount;

an extraction unit which extracts the partial regions of the first, second, third and fourth three-dimensional image data using a threshold related to bone;

a positional deviation correcting unit that corrects the third three-dimensional image on the basis of the calculated second positional deviation amount and creates fifth three-dimensional image data, and a processing unit that performs subtraction between the fifth three-dimensional image data and the first three-dimensional image data and creates sixth three-dimensional image data.

18. The three-dimensional image processing apparatus according to claim 14, wherein the partial region is a bone structure.

19. The three-dimensional image processing apparatus according to claim 18, wherein the bone structure is a skull base structure.

20. The three-dimensional image processing apparatus according to claim 14, wherein the positional deviation correcting unit specifies positional deviation of the second three-dimensional image with respect to the fourth three-dimensional image while shifting and/or rotating the second three-dimensional image with respect to the fourth three-dimensional image by a predetermined amount.

* * * * *